United States Patent [19]

Asano et al.

[11] Patent Number: 5,800,830

[45] Date of Patent: *Sep. 1, 1998

[54] BIFIDOBACTERIUM GROWTH PROMOTANT

[75] Inventors: Toshihiko Asano, Tsuchiura; Ryoko Kondo; Yasumi Mori, both of Tsukuba; Seishi Takenawa, Nara; Motoko Yamochi, Toyonaka; Kiyohiko Kunugita, Tsukuba; Tsutomu Terachi, Osaka, all of Japan

[73] Assignee: Fujisawa Pharmaceutical Co., Ltd., Osaka, Japan

[*] Notice: The term of this patent shall not extend beyond the expiration date of Pat. No. 5,605,697.

[21] Appl. No.: 758,516

[22] Filed: Nov. 29, 1996

Related U.S. Application Data

[63] Continuation of Ser. No. 325,183, filed as PCT/JP93/01473 Oct. 14, 1993, Pat. No. 5,605,697.

[30] Foreign Application Priority Data

| Oct. 27, 1992 | [JP] | Japan | 4/288643 |
| Mar. 5, 1993 | [JP] | Japan | 5/45022 |
| Mar. 9, 1993 | [JP] | Japan | 5/48354 |
| Mar. 11, 1993 | [JP] | Japan | 5/49805 |
| Mar. 22, 1993 | [JP] | Japan | 5/61721 |
| Mar. 23, 1993 | [JP] | Japan | 5/63765 |
| Mar. 23, 1993 | [JP] | Japan | 5/63972 |
| Mar. 23, 1993 | [JP] | Japan | 5/64222 |
| Mar. 24, 1993 | [JP] | Japan | 5/64451 |
| Mar. 24, 1993 | [JP] | Japan | 5/64560 |
| Mar. 26, 1993 | [JP] | Japan | 5/67892 |
| Mar. 31, 1993 | [JP] | Japan | 5/72695 |

[51] Int. Cl.$^6$ .............. A61K 47/12; A61K 9/68; A23L 1/222
[52] U.S. Cl. .............. 424/439; 424/440; 426/654
[58] Field of Search .............. 424/439, 440; 426/654

[56] References Cited

U.S. PATENT DOCUMENTS 5,605,697  2/1997  Asano et al. .............. 424/439

OTHER PUBLICATIONS

Shiotani et al., Chemical Abstracts, vol. 113, #114091, 1990.

*Primary Examiner*—Carlos Azpuru
*Attorney, Agent, or Firm*—Oblon, Spivak, McClelland, Maier & Neustadt, P.C.

[57] ABSTRACT

This invention relates to a bifidobacterium growth promotant comprising gluconic acid, a nontoxic salt thereof and/or glucono-δ-lactone as an active ingredient. The bifidobacterium growth promotant of this invention has selective bifidobacterial growth promoting-activity and, at the same time, inhibits growth of deleterious bacteria. Moreover, its rate of digestion and absorption in the upper alimentary tract is so low that the promotant has very satisfactory characteristics as a bifidus factor. Therefore, the bifidobacterium growth promotant of this invention can be used per se or as an additive for various foods and drink to provide functional foods and drinks, thus being of great value from the standpoint of health improvement.

8 Claims, No Drawings

BIFIDOBACTERIUM GROWTH PROMOTANT

TECHNICAL FIELD

This is a Continuation of application Ser. No. 08/325,183 filed on Apr. 24, 1995, now U.S. Pat. No. 5,605,697, which was filed as a 371 of International Application No. PCT/JP93/01473 filed on Oct. 14, 1993.

This invention relates to a growth promotant having a selective bifidobacterium growth promoting-effect and the use thereof in various applications.

BACKGROUND ART

Microorganisms of the genus Bifidobacterium, alias bifidobacteria, are constituents of the intestinal flora in mammals inclusive of man and it is known that these bacteria per se are not pathogenic but rather antagonizing pathogenic intestinal bacteria in respect of, for example, lactic acid production and nutrient requirement, thus interfering with proliferation of the pathogenic bacteria in the intestinal canal. It is also known that a breast-fed infant in whom these bacteria are present in the form of pure cultures is less susceptible to enteral infection than a bottle-fed infant in whom they are only sparsely present. Based on the above and other findings, many progresses have been made in the research concerning bifidobacteria of late and as more light is cast on the immuno-potentiating effect, prophylactic effect on microbial substitution, and inhibitory effect on carcinogenic substances of these bacteria, their clinical application has been attempted.

Since bifidobacteria must be encouraged to multiply in the intestine in order that their variegated actions may be exploited, much research into substances that could promote growth of bifidobacteria (hereinafter referred to as bifidus factors) is going on with great enthusiasm.

The generally acknowledged requisites of any bifidus factor are that it is not digested and absorbed in the upper digestive tract but reaches the ileum and large intestine and that it is efficiently assimilated by bifidobacteria and hardly utilized by other bacteria. Several substances in the name of bifidus factors have heretofore been proposed and, above all else, incorporation of oligosaccharides in various kinds of foodstuffs is broadly practiced.

However, from the standpoint of said requisites, the oligosaccharides so far reported are not impeccable bifidus factors. Fructooligosaccharides, for instance, have the disadvantage that they are decomposed by gastric acid and partly absorbed from the upper digestive tract. Isomaltooligosaccharides, too, are hydrolyzed by small intestine mucosal enzymes and absorbed there, thus making it mandatory to ingest them in massive doses. Galactooligosaccharides are relatively resistant to acid and heat and not easily digested and absorbed in the upper digestive tract but have the drawback, process-wise, that their yields are low and the costs of production are high. Furthermore, since all of them are sugars, they act as sweeteners when applied to food so that the disadvantage of sweetness alone being emphasized in the food is unavoidable. In addition, the utilization selectivity of bacteria for these saccharides is low. That is to say they are utilized not only by bifidobacteria but also by other intestinal bacteria, thus presenting the problem that a massive intake is necessary for achieving sufficient efficacy.

Having been developed with a view to overcoming the above-mentioned disadvantages of the prior art, this invention has for its object to provide a bifidus factor which is not digested and absorbed in the upper digestive tract, promotes growth of bifidobacteria remarkably, and does so with high selectivity.

DISCLOSURE OF INVENTION

This invention, made to accomplish the above object, is directed essentially to the incorporation of gluconic acid, a nontoxic salt thereof and/or glucono-δ-lactone as an active substance.

The inventors of this invention did intensive research about bifidus factors and discovered that gluconic acid, a nontoxic salt thereof and/or glucono-δ-lactone has activity to promote growth of bifidobacteria with good selectivity and, based on this new finding, did further research. This invention has been developed on the basis of the above research. Thus, the inventors' research into the bacterial utilization of gluconic acid revealed that said substance is efficiently utilized by *Bifidobacterium adolescentis*, among bifidobacteria, which is reportedly predominant in the intestinal tract of the adult human and is not utilized by *Clostridium perfringens*, which is a causative agent of puerperal fever, appendicitis, enteritis and food poisoning, but rather inhibits its growth. It was also elucidated that gluconic acid (salt) is not utilized by bacteria of the genus Bacteroides which are said to be dominant in the intestine.

It is described in Bergy's Manual of Systematic Bacteriology, 8th ed., the Williams and Wilkinson, that gluconic acid (salt) is utilized by *Bifidobacterium adolescentis* in vitro. Whereas, as mentioned above, an important requisite of a bifidus factor is that it is not digested and absorbed in the upper digestive tract but reaches the large intestine, it is known that organic acids in general are absorbed in the small intestine, suggesting that gluconic acid would also be absorbed in the small intestine. Moreover, since gluconic acid resembles glucose in chemical structure, it has been believed that like glucose it is absorbed in the small intestine. However, as described hereinafter, an experiment about the small intestinal absorption of gluconic acid under the conditions providing for 100% absorption of glucose in the intestinal loop assay revealed surprisingly that a major proportion of gluconic acid is not absorbed in the small intestine but reaches the large intestine. It is a new finding that an organic acid has activity to promote the growth of bifidobacteria. In addition, the inventors of this invention should be credited with the discovery that gluconic acid inhibits growth of *Clostridium perfringens* which is termed "harmful bacteria." Thus, gluconic acid has activity to promote selective growth of bifidobacteria.

Among species of bifidobacteria, it is known that not only said *Bifidobacterium adolescentis* but also *Bifidobacterium pseudocatenulatum*, *Bifidobacterium catenulatum*, etc. are capable of utilizing gluconic acid. Therefore, gluconic acid, a nontoxic salt thereof and glucono-δ-lactone are able to promote growth of these bacteria.

Since gluconic acid has a mild sour taste, it is used as a food acidulant, and because its calcium salt is readily soluble in water, it has been used as a calcium or supplement for food or medicinal use. Glucono-δ-lactone, when dissolved in water, converts itself gradually to gluconate and is in use as a coagulant in the production of soybean curds and baking powder of bread.

The nontoxic salt of gluconic acid for use in this invention is not restricted, inasmuch as it is physiologically harmless and efficiently utilized by bifidobacteria. Thus, alkali metal salts, e.g. sodium salt, potassium salt, etc., calcium salt, magnesium salt, zinc salt, copper salt, etc. can be mentioned as preferred examples.

Gluconic acid, a salt thereof and/or glucono-δ-lactone, which as aforesaid has activity to promote growth of bifidobacteria, can be used as a bifidobacterium growth promotant, a Clostridium growth inhibitor, an intestinal function controlling agent, an intestinal putrefactive fermentation inhibitor, a prophylactic and therapeutic agent for diarrhea, a stool deodorant, a stool property improving agent or an anticonstipation drug in man and animals, and even as an animal growth promotant, among other uses.

A variety of compositions for diverse uses, inclusive of those for use as a bifidobacterium growth promotant in accordance with this invention can be provided in a variety of dosage or application forms such as powders, granules, tablets, etc. each containing gluconic acid, a nontoxic salt thereof and/or glucono-δ-lactone, optionally in combination with other bifidobacterium growth promotant. Depending on specific uses and objectives, such compositions can be provided in liquid forms.

Furthermore, the compositions for various uses, inclusive of those for use as a bifidobacterium growth promotant, according to this invention may contain a variety of conventional additives with advantage. Included among such additives are dietary fibers such as apple pulp fiber, corn fiber, alginic acid, carrot powder, pectin, seaweed polysaccharide, carboxymethylcellulose, etc.; excipients such as lactose, starch, etc.; sweeteners such as sucrose, maltose, fructose, sorbitol, mannitol, stevioside, aspartame, etc.; nutritional supplements such as vitamins, minerals, skim milk, meat extract, etc.; flavors; binders such as gum arabic powder, polyvinylpyrrolidone, hydroxypropylcellulose, etc.; and lubricants such as magnesium stearate, calcium stearate, talc, etc.; among other additives. These additives can be selectively employed.

The bifidobacterium growth promotant or other compositions of this invention can be administered to man and animals either in the form of gluconic acid, a nontoxic salt thereof and/or glucono-δ-lactone as such or in the form of a suitable preparation. As a further alternative, they can be added to food for human consumption or feed for animals.

To be specific, they can be added to fermented milk, soft drinks, sherbets, candies, jellies and other confectioneries, soybean curds, meat and fish cakes and sausages, and other foods (e.g. various pickles, dressings, etc.). Also, for the purpose of a stool deodorant, said compositions can be added to diets for the aged or to hospital rations. The powders and granules can be added to fish flour, instant soup, instant "miso" soup, etc. moreover, for the prophylaxis and therapy of diarrhea, attenuation of fecal odor, or growth promotant, it can be used as feed additive for cattle, swine, poultry and other domestic animals and pet animals such as the dog and cat. As a further mode of use, gluconic acid, a nontoxic salt thereof and/or glucono-δ-lactone can be added to drinking water for man and animals.

Furthermore, while gluconic acid, a nontoxic salt thereof and/or glucono-δ-lactone has already been in use as an acidulant, calcium supplement (calcium gluconate), coagulant, or baking powder, it can be used as a bifidus factor additionally having the functions of such agents.

The preferred concentration in food or feed is 0.1–10 weight %. While the nontoxicity of gluconic acid is well known, the daily total intake can be about 0.1 g/kg for adults and about 0.05 g/kg for infants and children as rule of thumb.

The various effects, inclusive of the effect of promoting growth of bifidobacteria, of this invention can also be expected from the use of those substances which are hydrolyzed to liberate gluconic acid in water, such as various esters of gluconic acid (e.g. alkyl esters such as methyl ester, ethyl ester, etc.), glucono-γ-lactone, etc. or even from the use of D-galactonic acid, D-galacto-1,4-lactone and so on.

The food and food materials containing gluconic acid, a nontoxic salt thereof and/or glucono-δ-lactone, which has a selective growth promoting effect on bifidobacteria, are of use as functional foods and food materials.

With regard to means for containing gluconic acid, a nontoxic salt thereof or glucono-δ-lactone in a substrate food or food material, a direct addition method and a method which comprises causing a component of a food or food material to be chemically or biochemically converted to gulconic acid can be utilized.

When the former method is employed, a suitable member can be selected from among gluconic acid, a nontoxic salt thereof and glucono-δ-lactone according to the specific objective. Thus, for example, where the objective is addition of a sour taste, gluconic acid and/or glucono-δ-lactone or an equivalent thereof can be added. For the purpose of addition of a salty taste or improving the taste, the addition of sodium gluconate and/or potassium gluconate may be reasonably contemplated. Where the latter method is employed, supposing that the food or food material contains glucose, an enzyme such as glucose oxidase or a gluconic acid-producing microorganism may be used on the food or food material to convert to gluconic acid. In the event the food or food material contains sucrose or starch, a method that can be used comprises causing an enzyme such as invertase or amylase to produce glucose and, then, converting the glucose to gluconic acid in the same manner as above.

The food and food materials in which gluconic acid, a nontoxic salt thereof and/or glucono-δ-lactone can be contained are not limited to the above-mentioned kinds of foodstuffs but encompasses the entire spectrum of foods and food materials including sweeteners, honey, royal jelly, dairy products, soybean products, table salt, acidulants, condiments, starch, dextrin, processed animal or fish meat, noodles, beverages, bread, cakes, confectioneries, salted foods such as pickles, pH control agents, freezing-point depressants for controlled freezing-point storage, moisture activity depressants, preservatives, excipients, diluents/volume builders, and so on. Some representative foods and food materials, among those mentioned above, are now explained.

(1) Honey

Honey contains a small amount of gluconic acid but in order that the bifidobacterial growth promoting activity of gluconic acid may be overtly expressed, its concentration must be increased. In consideration of the fact that the sweet taste of honey blends well with the sour taste of gluconic acid, a novel type of honey with a hint of sour taste can be produced by adding gluconic acid or glucono-δ-lactone to honey or converting the glucose occurring in honey enzymatically to gluconic acid.

(2) Sweeteners

Sweeteners such as isomerized syrup, starch syrup, brown sugar and glucose are frequently used in beverages, candies and confections. These sweeteners can be modified and converted to novel functional sweeteners having a sour taste by adding gluconic acid and/or glucono-δ-lactone or converting their ingredients partly to gluconic acid.

(3) Oligosaccharides

Oligosaccharides having various functional characteristics have been developed. By adding gluconic acid, a nontoxic salt thereof and/or glucono-δ-lactone to such oligosaccharides to amplify their functionalities, novel gustatory sweeteners can be provided.

(4) Dairy Products

Milk and skim milk are in use as raw materials for a variety of foods. By adding gluconic acid, they can be made into novel gustatory functional food materials.

Aside from the above mentioned uses, gluconic acid, a nontoxic salt thereof and/or glucono-δ-lactone may be included in all kinds of foods and food materials and can be used selectively according to objectives, e.g. addition of a sour or salty taste or for calcium or magnesium supplementation.

Moreover, alkali metal salts of gluconic acid which, as aforesaid, have bifidobacterial growth promoting activity possess for the following additional effects.

(1) When used in combination with aspartame, they improve the sweetness of aspartame.
(2) When used in combination with a coagulant for the production of a soybean curd, they do not influence on the flavor and texture of the soybean curd.
(3) When used in combination with common salt, they improve the taste of sodium chloride and do not deteriorate its preservative effect.

Furthermore, gluconic acid has an action to impart a function to acidulants heretofore in use without deteriorating their native gustatory quality, flavor and intensity of sour taste.

These aspects are now explained in detail.

A functional sweetener containing aspartame and an alkali metal gluconate:

Aspartame (α-L-aspartyl-L-phenylalanine methyl ester; hereinafter referred to as aspartame) is about 100–200 times as sweet as sucrose and when used in food, its low energy feature can be exploited with advantage and, hence, aspartame is in broad use as a diet sweetener in a variety of beverages and cakes, among others. Its quality of sweetness is comparatively akin to that of sucrose but aspartame has the defect that its sweetness is slightly delayed in onset and tends to remain longer on the tongue. Therefore, means for ameliorating these aspects have been explored. For example, the use of aspartame in combination with cyclodextrin (JP Kokai S-60-114166) and the use of aspartame in combination with corn syrup (JP Kokai S-60-114167) are known. However, since cyclodextrin and corn syrup are digested and absorbed, thus functioning as energy sources, these methods are not satisfactory from the consideration of low energy formulation.

Meanwhile, it is known that alkali metal salts of gluconic acid improve the taste of the synthetic sweetener acesulfame K (JP Kokai S-59-66857) but the literature is reticent about the ways in which an alkali metal gluconate actually improves the taste.

The inventors explored for means by which the gustatory quality of aspartame may be brought as close as possible to that of sucrose without detracting from its characteristics and found that the above object can be accomplished by using aspartame in combination with an alkali metal salt of gluconic acid. Thus, an alkali metal gluconate added in a small amount improves the quality of sweetness of aspartame so that there is provided a sweetener composition comprising aspartame and alkali metal gluconate which has a low caloric value and yet encourages selective growth of bifidobacteria, thus being very satisfactory from health points of view and, hence, of value as a functional sweetener.

The functional sweetener of this invention can be used for sweetening all types of foods.

Regarding the amount of such alkali metal gluconate, an improving effect on the quality of sweetness can be obtained at the level of addition of at least one equivalent with respect to each weight part of aspartame but when the added amount of the alkali metal gluconate is too excessive, a salty taste will be developed. Therefore, the level of addition should be adjusted according to each type of food. For example, in the case of certain foods in which salty taste is disagreeable, such as soft drinks, the concentration of the alkali metal gluconate therein is preferably not higher than 1%. Conversely in the case of foods which should be both sweet and salty taste, such as pickles, it is not objectionable at all even if the concentration of the alkali metal gluconate exceeds 1%.

Regarding the mode of use of the sweetener of this invention, aspartame and an alkali metal gluconate may be independently added to food or alternatively a premix of aspartame and alkali metal gluconate, prepared for the particular kind of food, may be added to the food. As to the application form of the sweetener, ordinary application forms such as powders, granules, liquids etc. can be utilized. It is also permissible to incorporate various auxiliary components such as acidulants, other sweeteners, condiments, excipients, etc. in addition to aspartame and alkali metal gluconate.

The functional sweetener of this invention is such that the taste of aspartame has been brought as close as possible to that of sucrose and that it is not only an excellent low-energy sweetener but also a functional sweetener because it provides for selective growth of intestinal bifidobacteria as the effect of the alkali metal gluconate contained.

A functional coagulant prepared by adding an alkali metal gluconate to the coagulant for soybean curds:

While a soybean curd is manufactured by adding a coagulant to soy milk from soybeans, the conventional coagulant, glucono-δ-lactone is disadvantageous in that, when dissolved in water, it is hydrolyzed to gluconic acid so that when this coagulant is used in excess, a sour taste is imparted to the product curd. In this sense, the highest permissible level of addition is considered to be 0.3%.

Development of functional foods is in progress to keep abreast of the increasingly health-oriented mind of the public and, if only because it is a traditional food, it should be of great significance if soybean curds could be provided with a new function.

Based on the above-mentioned new finding that gluconic acid or its equivalent has activity to promote growth of bifidobacteria, the inventors of this invention did much research to accomplish the above-mentioned object and found that by adding an alkali metal salt of gluconic acid in the course of production of a soybean curd, a functional soybean curd containing gluconic acid or its equivalent in a high concentration can be manufactured without detracting from the native flavor and texture of soybean curds. As the coagulant for soybean curds that can be used, there can be mentioned the conventional coagulants for soybean curds, for example glucono-δ-lactone, calcium gluconate, calcium sulfate, and magnesium chloride, inclusive of their premixes.

The ratio of alkali metal gluconate to coagulant in the functional coagulant which can be prepared by adding the alkali metal gluconate to the conventional coagulant for soybean curds can be generally about 0.3 to 30 parts to each part of the coagulant.

In manufacturing a soybean curd using such a functional for coagulant soybean curd containing an alkali metal gluconate, the amount of said conventional coagulant can be just enough to cause coagulation of soy milk but it is generally preferable that the amount of gluconic acid in the product soybean curd be not less than 0.5% (% by weight; the same applies hereinafter).

Furthermore, in the manufacture of a soybean curd, salts of other organic acids, such as sodium malate, sodium citrate, etc., are sometimes used in addition to the coagulant.

The level of addition of alkali metal gluconate is not so strict but when functionality is taken into consideration, it is preferably added at a final concentration of at least 0.5% as gluconic acid in the soybean curd. Where glucono-δ-lactone and/or calcium gluconate or a composition containing either of them or both is used as the coagulant, the amount of alkali metal gluconate is preferably adjusted so that the total concentration as gluconic acid will be at least 0.5%.

The alkali metal gluconate can be added in any appropriate stage of soybean curd production. One examplary method of addition comprises adding said salt to the "go" obtained by milling soybeans in water or to the soy milk available on removal of insoluble residue following the heat-treatment of "go". As to the manner of addition, the gluconate may be added either singly or in the form of a premix containing various additives such as the antifoam and coagulant, which are commonly employed in the manufacture of soybean curds, and/or other food materials.

The alkali metal gluconate can be used in all types of soybean curds, including "kinugoshi tofu", "prepacked tofu", "momen tofu", "soft tofu" and so on. In each case, the coagulants (e.g. glucono-δ-lactone, calcium sulfate, magnesium chloride, etc.) and other additives which are conventionally used in the production of the respective types of soybean curds can be used.

The functional soybean curd of this invention is of value in the sense that by adding a gluconic acid compound such as an alkali metal gluconate to the conventional soybean curd, the soybean curd is provided with a new function of promoting growth of bifidobacteria without affecting the inherent flavor and texture of soybean curds.

A functional salt prepared by adding an alkali metal gluconate to common salt:

It is said that the recent increase in the incidence of various adult diseases is significantly related to dietary life and, as one of the etiologic factors involved, a causal relationship of sodium chloride intake to hypertension has been pointed out. As a countermeasure, a variety of low-salt foods have appeared on the market for reducing sodium chloride intake. However, it is not true that sodium chloride is used for the sole purpose of adding a salty taste to food but, in many instances, the salt plays significant roles in the processing and preservation of food. For example, warnings are being voiced against the ill effect of reduced salt contents on the processing characteristics and shelf-life of pickles owing to the insufficient osmolarity and increased water activity.

To overcome the above disadvantage, such means as using potassium chloride to make up for a reduction in sodium chloride content or adding an acidulant, such as vinegar or an organic acid, have been practiced but all affect the taste of food significantly and, therefore, none can be said to be effective means. Under the circumstances, development of an additive capable of reducing the sodium chloride without affecting the taste and shelf-life of salt-formulated foods has been awaited in earnest.

As the result of the intensive research done for solving the above problems, it was found that although alkali metal salts of gluconic acid are less salty than sodium chloride, their taste is quality-wise close to that of sodium chloride so that these salts can be effective substitutes for common salt. Moreover, it was discovered, as mentioned above, that the gluconic acid compound is only sparingly absorbed in the small intestine and mostly reaches the large intestine where it selectively promotes growth of bifidobacteria, suggesting that it is not only of use as a substitute for sodium chloride but is beneficial in that it controls intestinal function. This invention provides a novel salting agent having the function of promoting growth of bifidobacteria without detracting from the quality of saltiness and shelf-life of salt-formulated foods.

The amount of alkali metal gluconate is not so critical. Thus, even if half or more of the usual amount of sodium chloride is replaced with an alkali metal gluconate, there is no untoward effect on the taste of food and at a substitution rate of 40% or more the gluconate rounds off the taste of sodium chloride so that its addition is effective in this respect, too.

With regard to the manner of use, it may be added independently of common salt or in the form of a premix. In addition, various other components such as acidulants, condiments, sweeteners and excipients can also be included in formulations.

The relative intensities of saltiness of sodium gluconate and potassium gluconate are shown below.

Their amounts to be added can be determined by consulting these values according to the intended intensity of saltiness of the product food.

TABLE 1

| | Intensity of salty taste (calculated from the threshold value) |
|---|---|
| | Saltiness index* |
| Sodium chloride | 1 |
| Sodium gluconate | 0.2 |
| Potassium gluconate | 0.15 |

*The relative value with the intensity of saltiness of sodium chloride being taken as unity.

In using an alkali metal gluconate as a salting (saltiness-imparting) agent, its specific uses are virtually unlimited and it can be used in all kinds of foods in which sodium chloride is conventionally formulated. Thus, for example, pickles, noodles, bread, "miso", soy source, salted fish or shellfish, soups, "miso" soup, etc. can be mentioned. Moreover, if the sole object is to impart saltiness to food, it is not always necessary to use sodium chloride in conjunction but an alkali metal gluconate alone can be added.

The functional salt of this invention is of value as a functional saltiness in the sense that an alkali metal gluconate added to food in various uses for which sodium chloride is conventionally added provides for an additional function of promoting growth of bifidobacteria without detracting from the quality of saltiness and shelf-life of the food.

A functional acidulant prepared by adding gluconic acid to an acidulant:

As substances which impart sourness to food, that is to say acidulants, a variety of organic acids have been employed but since each of them has its own taste and intensity of sourness, these acidulants are being selectively used according to types of foods. Thus, they are used in ways taking advantage of their respective characteristics; for example citric acid is frequently used in juices, tartaric acid in candies, and acetic acid in pickles. Moreover, in some types of foods, more than one acidulants are used in combination.

While development of functional foods is the order of the day, better acidulants would be provided if new functions could be added to the conventional acidulants as well.

The inventors of this invention did much research to that end and found that by adding gluconic acid to the conventional acidulant on the strength of the above-mentioned discovery of the growth promoting effect of gluconic acid on bifidobacteria, the new function can be imparted to the acidulant without adversely affecting the inherent characteristics, namely taste, flavor and sourness, of said acidulant. This finding was followed by further investigations which have resulted in the development of this invention herein disclosed.

This invention provides a novel acidulant having the function of promoting growth of bifidobacteria without detracting from the taste, flavor and intensity of sourness of the conventional acidulant through partial substitution of gluconic acid for said acidulant and a food containing said novel acidulant.

Gluconic acid for use in this invention includes, besides gluconic acid as such, any substance that gives gluconic acid in aqueous solution, for example glucono-δ-lactone, glucono-γ-lactone and alkyl esters of gluconic acid, such as ethyl gluconate. Generally, however, gluconic acid and glucono-δ-lactone, both of which are approved food additives, are preferably employed.

As to the acidulant, this invention is applicable to all types of acidulants heretofore in use as food acidulants, namely citric acid, lactic acid, tartaric acid, malic acid, acetic acid and succinic acid, to name but a few.

For partial substitution of gluconic acid for such an acidulant, their ratio depends on the type and intensity of sourness (degree of sourness) of the acidulant. The upper limit substitutability values for the respective organic acids (the relative amounts of gluconic acid that can be added without affecting the taste, flavor and intensity of sourness of the conventional acidulants) are shown on an equivalent sourness basis below (Table 2). The values shown correspond to cases in which gluconic acid as such is added and when any of said gluconic acid precursors is employed, the amount of gluconic acid formed in aqueous solution should be used as the basis of conversion. For reference's sake, the degrees of sourness of various acidulants with the degree of sourness of gluconic acid being taken as unity are shown (Table 3).

TABLE 2

| Acidulant | Upper limit substitutability values of gluconic acid (on an equivalent sourness basis) |
| --- | --- |
| Citric acid | 40% |
| Lactic acid | 30% |
| Tartaric acid | 40% |
| Malic acid | 30% |
| Acetic acid | 20% |
| Succinic acid | 50% |

TABLE 3

| Organic acid | Degree of sourness |
| --- | --- |
| Gluconic acid | 1 |
| Citric acid | 3 |
| Lactic acid | 3.2 |
| Tartaric acid | 4.7 |
| Malic acid | 4.1 |

TABLE 3-continued

| Organic acid | Degree of sourness |
| --- | --- |
| Acetic acid | 4 |
| Succinic acid | 3.6 |

The manner of reading the above tables is now explained taking citric acid as an example.

It can be seen from the above tables that when citric acid is added in an amount corresponding to 60% of its specification amount and gluconic acid is added in an amount corresponding in sourness to 40% of said specification amount, the result is not much different from the result obtainable by singular use of citric acid in terms of taste, flavor, and intensity of sourness. For example, for 40% replacement of the sourness of 0.5% citric acid with gluconic acid, citric acid and gluconic acid can be added at concentrations of 0.3% and 0.6%, respectively.

With regard to the manner of use of gluconic acid, it can be added independently of various acidulants or used in the form of a premix. The percentage of gluconic acid in such usage is preferably not greater than the value shown in terms of the degree of sourness in the above table. If gluconic acid is used in an amount exceeding the above value, it may happen that the taste and flavor of the acidulant are modified so that its native characteristics may not be exploited. Moreover, when more than one acidulants are used in combination, the formulation amount can be calculated with reference to the above-mentioned upper limit gluconic acid-substitutability values based on the degrees of sourness of the respective acidulants.

Then, as the most desirable examples of the functional acidulant obtainable by adding gluconic acid to a conventional acidulant, the acidulant comprising citric acid and gluconic acid in a ratio of 10:3~ 10:20, the acidulant comprising tartaric acid and gluconic acid in a ratio of 10:5~10:30, and the acidulant comprising lactic acid and gluconic acid in a ratio of 10:3~10:15 can be mentioned. These acidulants can be used singly or as a combination of two or more species according to the substrate food. For example, when one or more of these acidulants are to be added to a juice or a candy, the level of addition may be not less than 0.5% by weight.

The functional acidulant of this invention comprising a conventional acidulant and gluconic acid is of value as a function-oriented acidulant having an additional function of promoting growth of bifidobacteria without detracting from the well-known characteristic required of acidulants, whether in taste, in flavor or in the intensity of sourness.

Some test examples and working examples of this invention are presented below.

TEST EXAMPLE 1

<Gluconic Acid Absorption Test by the Intestinal Loop Method>

The test was performed using sodium gluconate as an example of this invention and glucose as a control. As experimental animals, a total of 12 rats (Wistar strain, male, aged 7 weeks, body weights 280 g, approx.) were divided into 4 groups.

Each experimental rat was fasted for 24 hours and then, under ether anesthesia, a loop about 10 cm long was formed of the upper part of the small intestine (the lower part of jejunum below the ligament of Treitz) or the lower part of the small intestine (ileum). The loop was infused with 0.5 ml of 100 mM sodium gluconate-saline or glucose-saline and the intestine was closed for 30 minutes' absorption. The loop was then excised and the internal fluid was washed out with 20 ml of saline.

The residual gluconic acid in the saline wash was assayed using F-Kit D-Gluconic Acid (Boehringer-Mannheim-Yamanouchi) and the glucose was assayed with Glucose C II Test Wako (Wako Pure Chemicals) and the respective values were recorded as dose-recovery amounts.

Moreover, on the occasion of said excision of the loop, the adjacent portion of the small intestine was additionally excised to prepare a loop (about 10 cm) for an addition-recovery experiment. This loop was infused with 0.5 ml of the test solution and the internal liquid was recovered and determined for gluconic acid or glucose in the same manner as above. Using the value thus found as the addition-recovery amount, the percent residue of each sample was calculated by means of the following equation.

$$\text{Residue }(\%) = \frac{[(\text{dose-recovery amount})/(\text{addition-recovery amount})] \times 100}$$

TABLE 4

| Part of small intestine | Upper part | Lower part |
|---|---|---|
| | Glucose | |
| Residue (%)* | 0 ± 0 | 50.7 ± 6.0 |
| | Sodium gluconate | |
| Residue (%)* | 80.1 ± 4.8 | 89.4 ± 13.4 |

*: Mean ± S.D.

The percent residues in the upper and lower parts of the small intestine are shown in Table 4. It is apparent from Table 4 that about 80–90% of gluconic acid remained in the small intestine, suggesting that this compound was only partly digested and absorbed in the small intestine. In contrast, glucose was almost completely absorbed in the upper part of the small intestine and little reached the large intestine so that it cannot be expected to encourage growth of bifidobacteria.

TEST EXAMPLE 2

<Selective Utilization of Gluconate>

As shown in Table 5, Bifidobacterium adolescentis ATCC 15703 and Bifidobacterium adolescentis ATCC 15705 were used as representative bifidobacteria, Welch's bacillus (Clostridium perfringens GKK 16 and Clostridium perfringens CWiu) as harmful bacteria, and the genus Bacteroides (Bacteroides fragilis W-7) as dominant intestinal bacteria. GAM broth (Nissui Pharm. Co., Ltd.) was inoculated with the test strain and incubated anaerobically at 37° C. for 20 hours to prepare a preculture.

As test substances, sodium gluconate, fructooligosaccharide and glucose were used (Table 5). For use as the glycolysis test medium, the basal medium available on elimination of agar from the ½ formulation of the GAM semisolid without dextrose medium (Nissui Pharm. Co., Ltd.) was supplemented with 0.5 w/v % of the test substance and adjusted to pH 6.9.

The above test medium was inoculated with 0.01 v/v % of said preculture and incubated anaerobically at 37° C. for 20 hours. Then, the optical density (660 nm) and pH were determined. The medium was distributed in 5 ml aliquots into test tubes sized 18 mm in diameter. Anaerobic culture was carried out using Anaeropak (Mitsubishi Gas Chemical Co.). Measurement of optical density (OD) was performed over the test tube using Shimadzu Milton-Roy spectrophotometer "Spectronic 20A". The pH was directly measured using the glass electrode of the pH Meter HM-30S (Toa Dempa Kogyo). The result was compared with that of the basal medium control and the judgement that the test substance was utilized was made in the case of an increase in optical density (OD) or a depression of pH. The results are shown in Table 5.

In addition, using Bifidobacterium adolescentis ATCC 15703 as a representative strain, a similar test was performed for calcium gluconate. The results are shown in Table 6.

TABLE 5 (-1)

| Test substance | | Control (basal medium) | Sodium gluconate |
|---|---|---|---|
| Test strain | | | |
| Bifidobacterium | OD | 0.27 | 0.68 |
| adolescentis ATCC 15703 | pH | 6.04 | 5.22 |
| Bifidobacterium | OD | 0.15 | 0.66 |
| adolescentis ATCC 15705 | pH | 6.10 | 5.28 |
| Clostridium perfringens | OD | 0.27 | 0.23* |
| GKK 16 | pH | 6.46 | 6.43 |
| Clostridium perfringens | OD | 0.36 | 0.33* |
| CWiu | pH | 6.60 | 6.56 |
| Bacteroides fragilis | OD | 0.48 | 0.48 |
| W-7 | pH | 6.12 | 6.07 |

TABLE 5 (-2)

| Test substance | | Fruct-oligosac-charide | Glucose |
|---|---|---|---|
| Test strain | | | |
| Bifidobacterium | OD | 0.77 | 0.84 |
| adolescentis ATCC 15703 | pH | 4.32 | 4.23 |
| Bifidobacterium | OD | 0.80 | 0.76 |
| adolescentis ATCC 15705 | pH | 4.27 | 4.27 |
| Clostridium perfringens | OD | 0.40 | 0.95 |
| GKK 16 | pH | 6.01 | 4.99 |
| Clostridium perfringens | OD | 0.47 | 1.04 |
| CWiu | pH | 6.53 | 5.24 |
| Bacteroides fragilis | OD | 0.64 | 0.60 |
| W-7 | pH | 5.20 | 4.99 |

*: Decrease in OD as compared with control

TABLE 6

| Test substance | | Control (basal medium) | Calcium gluconate |
|---|---|---|---|
| Test strain | | | |
| Bifidobacterium | OD | 0.25 | 0.45 |
| adolescentis ATCC 15703 | pH | 6.81 | 5.39 |

It is apparent from Tables 5 and 6 that sodium gluconate and calcium gluconate both according to this invention are well utilized by bifidobacteria and that sodium gluconate is not assimilated but rather inhibits growth of Welch's bacillus. It is also clear that sodium gluconate is not utilized by bacteria of the genus Bacteroides which are dominant members of the intestinal flora, indicating that the growth factor of this invention is an excellent selective growth promotant. On the other hand, glucose is well utilized by bifidobacteria but, unlike this invention, utilized without selectivity. Moreover, glucose is almost completely absorbed in the upper part of the small intestine and cannot reach the large intestine as can be seen from Test Example 1, thus being not considered to be a satisfactory bifidus factor.

TEST EXAMPLE 3

<Effect of Glucono-δ-lactone on Human Fecal Flora>

Glucono-δ-lactone (a lactone of gluconic acid), an example of this invention, was administered to man and its effect on the intestinal flora and stool properties was investigated.

One healthy male adult volunteer (50 years old) was asked to ingest 9 g of glucono-δ-lactone daily in 3 divided doses and the intestinal flora in the stool was determined on day 0, day 10 and day 30 of ingestion and day 20 of washout after ingestion in accordance with the method of Mitsuoka (Tomotari Mitsuoka: Chonaikin-no-Sekai (A Color Atlas of Anaerobic Bacteria), Sobunsha, Tokyo, p. 53, 1984)). The results are set forth in Table 7. As to stool properties, the subject himself made a sensory evaluation of consistency, color and odor on a daily basis.

TABLE 7

| Microorganism | Logarithm of the viable count in each gram of feces The figure in parentheses represents the percentage (%) of the total count | | | |
|---|---|---|---|---|
| | Day 0 of intake | Day 10 of intake | Day 30 of intake | Day 20 of washout |
| Bifidobacterium | 9.5 (10) | 10.5 (65) | 10.7 (94) | 9.7 (19) |
| Bacteroidaceae | 10.2 (52) | 10.0 (22) | 9.3 (4) | 10.3 (69) |
| Eubacterium | 9.4 (8) | 9.6 (8) | 8.9 (1) | 9.5 (11) |
| Peptococcaceae (anaerobic streptococci) | 9.9 (30) | 9.3 (5) | 8.7 (1) | 8.7 (2) |
| C. perfringens (Welch's bacillus) | 7.0 | <3 | <3 | 3.6 |
| Enterobacteriaceae (inclusive of coliform bacteria) | 7.0 | 6.4 | 6.2 | 6.8 |
| Total viable count | 10.5 (100) | 10.6 (100) | 10.7 (100) | 10.4 (100) |

It is apparent from Table 7 that the population of bifidobacteria inhabiting the intestinal tract was remarkably increased by glucono-δ-lactone. In contrast, the viable count of bacteria of the family Bacteroidaceae was decreased and the count of Welch's bacillus also fell below the detection limit. The stool was softened, intestine movement improved, and fecal odor suppressed.

TEST EXAMPLE 4

<Attenuation of Canine Fecal Odor>

Glucono-δ-lactone, as an example of this invention, was administered to dogs and its fecal deodorizing effect was evaluated.

Eight male beagle dogs aged about 10 months (body weights 10–13 kg) were divided into two groups of 4 to provide a glucono-δ-lactone treatment group and a glucono-δ-lactone-free control group.

Glucono-δ-lactone was filled in gelatin capsules and administered in a dose of 50 mg/kg body weight 3 times a day at 10 o'clock, 13 o'clock and 16 o'clock for 2 consecutive weeks. Before administration and at 2 weeks of administration, fresh feces in the treatment group and control group were respectively collected and the fecal odor was organoleptically evaluated by the sensory test.

Attenuation of fecal odor was obtained in the glucono-δ-lactone treatment group.

TEST EXAMPLE 5

<Sensory Test of Sweeteners>

The degree of improvement in sweetness on addition of sodium gluconate to aspartame was evaluated by a sensory test.

Method of the sensory test

A 10% solution of sucrose (x), a 0.083% solution of aspartame (y), and a solution (z) prepared by adding 0.3% of sodium gluconate to a 0.083% solution of aspartame were paired and it was evaluated how much the taste (A) of the first-tasted solution was close to the taste of sucrose as compared with the taste (B) of the second-tasted solution in accordance with the following criteria. It was ensured that the intensity of sweetness would be uniform over x, y and z and a 10% solution of sucrose was used as control.

The panel consisted of 10 tasters

| Compared with B, A is | |
|---|---|
| very close to control | +3 |
| fairly close to control | +2 |
| slightly close to control | +1 |
| Eqivocal | 0 |
| Compared with A, B is | |
| slightly close to control | −1 |
| fairly close to control | −2 |
| very close to control | −3 |

Result

TABLE 8

| First | Second | +3 | +2 | +1 | 0 | −1 |
|---|---|---|---|---|---|---|
| x | y | 5 | 3 | 2 | 0 | 0 |
| y | x | 0 | 0 | 0 | 0 | 1 |
| x | z | 0 | 2 | 7 | 0 | 1 |
| z | x | 0 | 0 | 2 | 0 | 6 |
| y | z | 0 | 0 | 1 | 0 | 1 |
| z | y | 4 | 3 | 1 | 1 | 1 |
| Total | | 9 | 8 | 13 | 1 | 10 |

| First | Second | −2 | −3 | Total score | Average score |
|---|---|---|---|---|---|
| x | y | 0 | 0 | 23 | 2.3 |
| y | x | 4 | 5 | −24 | −2.4 |
| x | z | 0 | 0 | 10 | 1.0 |
| z | x | 2 | 0 | −8 | −0.8 |
| y | z | 6 | 2 | −18 | −1.8 |
| z | y | 0 | 0 | 18 | 1.8 |
| Total | | 12 | 7 | | |

Analysis of variance of the above data showed significant differences among x, y and z but the quality of sweetness of (z), i.e. aspartame plus sodium gluconate, was significantly close to that of sucrose (x) as compared with aspartame alone (y), indicating an overt taste-improving effect. The relationship of the tastes of sucrose, aspartame and aspartame plus sodium gluconate is diagrammatically illustrated below.

| Aspartame (y) ↓ −1.38 | Aspartame + sodium gluconate (z) ↓ 0.30 | Sucrose (x) ↓ 1.08 |
|---|---|---|
| −1.5    −1.0    −0.5    0    0.5    1.0 | | |

For example, when the relationship of these three tastes is expressed by assigning 100 to the taste of sucrose and 0 to the taste of aspartame, the taste of aspartame plus sodium gluconate is 68, which means a marked improvement.

EXAMPLE 1

(Sweetener)

An orange fruit drink was prepared by adding water, citric acid and a sweetener composed of aspartame and alkali metal gluconate to a commercial 100% orange juice. As a comparison example, an orange juice drink was similarly prepared using a sufficient amount of granulated sugar to provide the same degree of sweetness. Then, the difference in taste between them was evaluated by the sensory test (triangle test). As a result, no significant difference was found between the invention and the comparison example.

| | Formulation of Example (A) | Formulation of Example (B) | Formulation of Comparison Example |
|---|---|---|---|
| 100% Orange juice | 150 g | 150 g | 150 g |
| Citric acid | 3.6 g | 3.6 g | 3.6 g |
| Aspartame | 0.22 g | 0.22 g | — |
| Sodium gluconate | 2.1 g | — | — |
| Potassium gluconate | — | 5.0 g | — |
| Granulated sugar | — | — | 51 g |
| Water | 516 g | 516 g | 516 g |

Sensory test
The panel consisted of 10 panelists.

TABLE 9

| Test group | | | Sensory test[Note] | |
|---|---|---|---|---|
| Example A | ←→ | Comparison Example | 5/10 | (no significant difference) |
| Example B | ←→ | Comparison Example | 5/10 | (no significant difference) |

[Note] Number of panelists giving the correct answer (discrimination)/number of panelists

EXAMPLE 2

(Honey)

To 200 g of Chinese milk vetch honey was added 300 g of water followed by addition of 0.5 g of an enzyme preparation containing glucose oxidase (60 units/mg) and catalase (390 units/mg) activities and the reaction was carried out at 23° C. under aerobic conditions for 90 minutes to provide a gluconic acid-containing honey. The result of assay of gluconic acid in this reaction mixture by high performance liquid chromatography is shown in Table 10.

This product has a refreshing gustatory quality possessing both a sour taste and a sweet taste.

TABLE 10

| | Before reaction | After reaction |
|---|---|---|
| Gluconic acid content (%) | 0.05 | 3.5 |
| pH | 4.2 | 2.6 |

EXAMPLE 3

(Isomerized Syrup)

To 135 g of isomerized syrup (42% fructose grade) was added 300 g of water followed by addition of 0.5 g of the same enzyme preparation as used in Example 2. The reaction was conducted aerobically at 23° C. for 90 minutes to provide a gluconic acid-containing isomerized syrup. The result of assay of gluconic acid in this isomerized syrup by high performance liquid chromatography is shown in Table 11.

TABLE 11

| | Before reaction | After reaction |
|---|---|---|
| Gluconic acid content (%) | 0.02 | 3.5 |
| pH | 5.8 | 2.5 |

For the production of a gluconic acid-containing isomerized syrup, it is an alternative reasonable procedure to conduct the above reaction upon completion of conversion of glucose to fructose in the process of isomerized syrup production and, thereafter, concentrate the reaction product.

EXAMPLE 4

(Glucose)

In 400 g of water was dissolved 100 g of glucose followed by addition of 0.5 g of the same enzyme preparation as used in Example 2. The reaction was then conducted aerobically at 23° C. for 90 minutes to provide a gluconic acid-containing glucose syrup. The result of assay of gluconic acid in this glucose syrup by high performance liquid chromatography is shown in Table 12.

TABLE 12

| | Before reaction | After reaction |
|---|---|---|
| Gluconic acid content (%) | 0 | 5.4 |
| pH | 6.7 | 2.6 |

EXAMPLE 5

(Corn Syrup)

To 100 g of corn syrup was added 400 g of water followed by addition of the same enzyme preparation as used in Example 2 and the reaction was carried out aerobically at 23° C. for 90 minutes to provide a gluconic acid-containing corn syrup. The result of assay of gluconic acid in this corn syrup by high performance liquid chromatography is shown below in the table. As in Example 3, it is also a reasonable procedure to conduct the above reaction upon completion of hydrolysis of starch in the process of corn syrup production to thereby provide a gluconic acid-containing corn syrup.

TABLE 13

|  | Before reaction | After reaction |
|---|---|---|
| Gluconic acid content (%) | 0.05 | 3.0 |
| pH | 4.2 | 2.8 |

EXAMPLE 6

(Oligosaccharide)

To 150 g of isomaltooligosaccharide (Isomalt 500, Showa Sangyo) was added 350 g of water followed by addition of 0.5 g of the same enzyme preparation as used in Example 2 and the reaction was conducted aerobically at 23° C. for 90 minutes to provide a gluconic acid-containing oligosaccharide syrup. The result of assay of gluconic acid in this oligosaccharide syrup by high performance liquid chromatography is shown in Table 14. As mentioned in Example 3, it is also a reasonable procedure to first conduct the isomaltooligosaccharide-producing enzymatic reaction in the process of oligosaccharide production, then conduct the above-described reaction, and finally concentrate the reaction mixture. Aside from the foregoing, fructooligosaccharide, galactooligosaccharide, lactosucrose, etc. can also be converted to the corresponding gluconic acid-containing oligosaccharides.

TABLE 14

|  | Before reaction | After reaction |
|---|---|---|
| Gluconic acid content (%) | 0.02 | 4.0 |
| pH | 3.6 | 2.5 |

EXAMPLE 7

(Brown Sugar)

To 100 g of brown sugar was added 400 g of water. Then, 0.1 g of invertase (4 U/ml) and 0.5 g of the same enzyme preparation as used in Example 2 were added and the reaction was conducted aerobically at 23° C. for 90 minutes to provide a gluconic acid-containing brown sugar syrup. The result of assay of gluconic acid in this brown sugar syrup by high performance liquid chromatography is shown in Table 15.

TABLE 15

|  | Before reaction | After reaction |
|---|---|---|
| Gluconic acid content (%) | 0 | 3.6 |
| pH | 5.8 | 3.0 |

EXAMPLE 8

(Milk Beverage)

To 20 g of skim milk was added 180 g of water followed by addition of 2 g of calcium gluconate and 3 g of sodium gluconate. This procedure provided a stable calcium-enriched milk drink giving no precipitation on heating.

EXAMPLE 9

(Coagulated Milk)

To 100 g of cow's milk were added 10 g of sugar and 3 g of glucono-δ-lactone and the mixture was heated at 80° C. for 30 minutes to coagulate the milk and provide a coagulated milk dessert food.

EXAMPLE 10

(Apple Juice Drink)

An apple juice was prepared by adding water, citric acid, granulated sugar and sodium gluconate to a commercial 100% apple juice. (The formulation is shown below).

Compared with the sodium gluconate-free juice, this product had a thick taste close to the taste of 100% apple juice.

| 100% Apple juice | 20 g |
|---|---|
| Granulated sugar | 8 g |
| Citric acid | 0.32 g |
| Sodium gluconate | 1.08 g |
| Water | 80 g |

EXAMPLE 11

(Soybean Curd)

To 200 g of soybeans which had been caused to absorb enough water by overnight soaking was added 350 ml of water and the mixture was milled in a mixer to prepare a "go". This "go" was steam-heated and after its temperature had reached 100° C., was further heated for 3 minutes. The "go" was then immediately passed through a filter cloth to remove the insoluble residues to provide a soy milk. To this soy milk was added sodium gluconate at a level of 0.6% or 1.0% followed by addition of 0.3% of glucono-δ-lactone. The mixture was heated on a water bath at 80° C. for 30 minutes to provide a soybean curd.

The results are set forth in Table 16.

The sodium gluconate-containing soybean curd thus obtained was more "substantial" and had a better taste than a sodium gluconate-free control soybean curd. Incidentally no remarkable difference was found in hardness and texture.

TABLE 16

| Amount of sodium gluconate (%) | Hardness[Note 1)] (g/0.5 cm$^2$) | Taste | Gluconic[Note 2)] acid content (%) |
|---|---|---|---|
| Control (not added) | 49 | — | 0.33 |
| 0.6 | 50 | More substantial than control | 0.87 |
| 1.0 | 47 | More substantial than control | 1.23 |

Note 1)Determined with a curd meter.
Note 2)As gluconic acid (calcd.)

EXAMPLE 12

(Soybean Curd)

A soy milk prepared in the same manner as in Example 11 was cooled to 20° C. and sodium gluconate was added at a final concentration of 1%. Then, glucono-δ-lactone was added at a concentration of 0.3% and the mixture was heated on a water bath at 90° C. for 40 minutes to provide a soybean curd.

The results are shown in Table 17.

The sodium gluconate-containing soybean curd thus obtained was more "substantial" and tasted better than the control soybean curd. Incidentally no remarkable difference was found in hardness and texture.

TABLE 17

| Amount of sodium gluconate (%) | Hardness (g/0.5 cm²) | Taste | Gluconic acid content (%) |
|---|---|---|---|
| Control (not added) | 57 | — | 0.33 |
| 1.0 | 56 | More substantial than control | 1.23 |

EXAMPLE 13

(Soybean Curd)

To a soy milk prepared in the same manner as in Example 11 was added sodium gluconate at a concentration of 1.0%. Then, a coagulant composed of 67% glucono-δ-lactone and 33% calcium sulfate was added at the level of 0.30 or 0.34%. The mixture was heated on a water bath at 80° C. for 30 minutes to provide a soybean curd. As control, 0.30% of the same coagulant as above was added to the sodium gluconate-free soy milk to provide a control soybean curd.

The results are shown in Table 18.

The sodium gluconate-containing soybean curd was slightly softer but its hardness could be made close to that of control by increasing the amount of coagulant.

TABLE 18

| Amount of sodium gluconate (%) | Amount of coagulant (%) | Hardness (g/cm²) | Taste | Gluconic acid content (%) |
|---|---|---|---|---|
| Control (not added) | 0.30 | 40 | — | 0.22 |
| 1.0 | 0.30 | 33 | More substantial than control | 1.12 |
| 1.0 | 0.34 | 39 | More substantial than control | 1.15 |

EXAMPLE 14

(Coagulant)

Three (3) kg of sodium gluconate was mixed with 1 kg of glucono-δ-lactone to provide 4 kg of a functional soybean curd coagulant.

EXAMPLE 15

(Coagulant)

One (1) kg of potassium gluconate was mixed with 300 g of glucono-δ-lactone to provide 1.3 kg of a functional soybean curd coagulant.

EXAMPLE 16

(Coagulant)

Three (3) kg of sodium gluconate was mixed with 600 g of glucono-δ-lactone and 400 g of calcium sulfate to provide 4 kg of a functional soybean curd coagulant.

EXAMPLE 17

(Soybean Curd)

To a soy milk prepared in the same manner as in Example 11 was added the functional soybean curd coagulant obtained in Example 15 at a concentration of 1.3% and the mixture was heated on a water bath at 80° C. for 30 minutes to provide a soybean curd. The soybean curd thus obtained had a very satisfactory taste without any deterioration in hardness, texture and other characteristics.

TEST EXAMPLE 6

(Sensory Test of Salting Agents)

Common salt and a salting agent prepared by partial substitution of sodium gluconate for common salt were used. The relative taste of aqueous solutions of the respective materials as prepared to the same intensity of saltiness was evaluated by a sensory test.

(Method of the Sensory Test)

An aqueous solution was prepared by dissolving the salting agent containing sodium gluconate (GNA) partially replacing common salt at a final concentration of 5% and an aqueous solution of common salt was also prepared to the same intensity of saltiness. The difference in taste between these two aqueous solutions was evaluated by a triangle test.

The results are set forth in the following table.

TABLE 19

| Test group | | | | Number of panelists giving the correct answer/total number of panelists[Note 1)] |
|---|---|---|---|---|
| Common salt | 3.5% | ⟵⟶ | Common salt 3.8% | 4/10 |
| GNA | 1.5% | | | |
| Common salt | 3.0% | ⟵⟶ | Common salt 3.4% | 7/10* |
| GNA | 2.0% | | | |
| Common salt | 2.5% | ⟵⟶ | Common salt 3.0% | 8/10** |
| GNA | 2.5% | | | |
| Common salt | 2.0% | ⟵⟶ | Common salt 2.6% | 8/10** |
| GNA | 3.0% | | | |

| Test group | | | | Quality of saltiness[Note 2)] |
|---|---|---|---|---|
| Common salt | 3.5% | ⟵⟶ | Common salt 3.8% | — |
| GNA | 1.5% | | | |
| Common salt | 3.0% | ⟵⟶ | Common salt 3.4% | GNA plus is milder 5 Common salt is milder 2 |
| GNA | 2.0% | | | |
| Common salt | 2.5% | ⟵⟶ | Common salt 3.0% | GNA plus is milder 7 Common salt is milder 1 |
| GNA | 2.5% | | | |
| Common salt | 2.0% | ⟵⟶ | Common salt 2.6% | GNA plus is milder 8 Common salt is milder 0 |
| GNA | 3.0% | | | |

Note 1)*: significant difference at 5% level
**: significant difference at 1% level
No mark: No significant difference
Note 2) Among the panelists giving the correct answer, the number of panelists who answered that the GNA plus was milder or that common salt was milder.

EXAMPLE 18

(Salting Agent)

To 300 g of cucumbers were evenly smeared with 15 g of a salting agent composed of 40% sodium chloride and 60% alkali metal gluconate. The cucumbers were then put in a tray and after placement of a cover in position, a weight of 600 g was placed on the cover. The cucumbers were allowed to stand in this condition at room temperature for 24 hours to provide overnight-pickled cucumbers. As a comparison example, overnight-pickled cucumbers were similarly prepared using 15 g of sodium chloride only as the salting agent. The overnight-pickled cucumbers obtained by using the gluconic acid salt was milder in saltiness than the comparison pickled cucumbers but there was no difference in appearance, texture, or degree of dehydration, indicating that the alkali metal gluconate can be a satisfactory substitute for common salt.

The results are set forth in Table 20.

TABLE 20

| Raw material | | | Overnight pickles | |
|---|---|---|---|---|
| Salting agent | | Cucumbers | Yield | Taste etc. |
| Common salt<br>Sodium gluconate | 6 g<br>9 g | 300 g | 260 g | Saltiness milder than Comparison Example. No difference in texture. |
| Common salt<br>Potassium gluconate | 6 g<br>9 g | 300 g | 263 g | Saltiness milder than Comparison Example. No difference in texture. |
| Common salt<br>(Comparison Example) | 15 g | 300 g | 264 g | — |

TEXT EXAMPLE 7

(Acidulant)

As acidulants, citric acid, lactic acid, tartaric acid, malic acid, acetic acid and succinic acid were selected and each of these basal acidulants and an acidulant prepared by substituting gluconic acid for part or all of the basal acidulant on an equivalent sourness basis were used. The maximum amount of gluconic acid that could be formulated with sensory test was determined on the basis of sourness.

Method of the sensory test:

Each acidulant as such (A) and an acidulant (B) prepared by substituting gluconic acid for part or all of acidulant (A) on an equivalent sourness basis were evaluated by the triangle test to see whether there was a sensory test difference. The number of panelists was 10.

Results:

The results are set forth in the following table.

TABLE 21

| | B<br>Degree of gluconic acid substitution<br>(% on a sourness basis) | | | | | |
|---|---|---|---|---|---|---|
| A | 20 | 30 | 40 | 50 | 60 | 100 |
| Citric acid | — | — | 4/10 | 7/10* | — | 8/10** |
| Lactic acid | — | 4/10 | 7/10* | — | — | 8/10** |
| Tartaric acid | — | — | 1/10 | 7/10* | — | 9/10** |
| Malic acid | — | 4/10 | 7/10* | — | — | 8/10** |
| Acetic acid | 3/10 | 7/10* | — | — | — | 10/10** |
| Succinic acid | — | — | — | 4/10 | 8/10** | 10/10** |

TABLE 21-continued

| | B<br>Degree of gluconic acid substitution<br>(% on a sourness basis) | | | | | |
|---|---|---|---|---|---|---|
| A | 20 | 30 | 40 | 50 | 60 | 100 |

Note 1) Each figure in the table denotes the number of panelists giving the correct answer (discrimination)/the total number of panelists.
*: Significant difference at 5% level
**: Significant difference at 1% level
No mark: No significant difference

EXAMPLE 19

(Acidulant)

An orange juice was prepared by adding water, granulated sugar and, as acidulants, citric acid and gluconic acid to a commercial 100% orange juice. As a comparison example, an orange juice drink was similarly prepared by using citric acid as acidulant to provide for the equivalent degree of sourness. The relative taste of both drinks was evaluated by the sensory test (triangle test). No significant difference in taste was found between the two drinks.

| Formulation of Example | |
|---|---|
| 100% orange juice | 150 g |
| Granulated sugar | 51 g |
| Citric acid | 2.16 g |
| 50% Gluconic acid | 8.64 g |
| Water | 509 g |
| Formulation of Comparison Example | |
| 100% orange juice | 150 g |
| Granulated sugar | 51 g |
| Citric acid | 3.6 g |
| Water | 516 g |

Sensory test: 10 panelists

The number of panelists giving the correct answer (discrimination)=4 (no significant difference)

EXAMPLE 20

(Acidulant)

A thick-walled cooking pan was charged with granulated sugar, corn syrup and water and heated over a slow fire. As the contents began to boil, the lid was placed in position and the pan was further heated. When the liquid temperature had reached 150° C., an aqueous solution of the acidulant composed of tartaric acid and gluconic acid was added and the fire was extinguished. The contents were transferred to a vat coated with salad oil and with the syrup being retained with a spatula, the syrup was allowed to cool uniformly. When the syrup had cooled, it was cut to size and rounded up to provide a candy. As a comparison example, a candy was similarly manufactured using tartaric acid as acidulant to the same sourness as the Example. No difference was found between the two candies in taste or testure.

| Formulation of Example | |
|---|---|
| Granulated sugar | 65 g |
| Powdered corn syrup | 4.3 g |
| Tartaric acid | 0.66 g |

| | |
|---|---|
| 50% Gluconic acid | 4.14 g |
| Water | 26.2 g |
| Formulation of Comparison Example | |
| Granulated sugar | 65 g |
| Powdered corn syrup | 4.3 g |
| Tartaric acid | 1.1 g |
| Water | 28.3 g |

EXAMPLE 21

(Acidulant)

A flavored vinegar prepared by mixing vinegar with gluconic acid, common salt and granulated sugar was added to cooked rice prepared in the conventional manner and after uniform blending, the rice was allowed to cool to provide a sushi rice stock for chirashi-zushi. As a comparison example, a sushi rice stock was similarly prepared using vinegar as acidulant to the same degree of sourness. The two sushi rice stocks organoleptically showed no significant difference in taste, flavor and texture.

| Formulation of Example | |
|---|---|
| Cooked rice | 300 g |
| Flavored vinegar: | |
| Vinegar | 16 g |
| 50% Gluconic acid solution | 1.44 g |
| Granulated sugar | 5 g |
| Common salt | 1.6 g |
| Formulation of Comparison Example | |
| Cooked rice | 300 g |
| Flavored vinegar: | |
| Vinegar | 20 g |
| Granulated sugar | 5 g |
| Common salt | 1.6 g |

TEST EXAMPLE 8

<Effect of Calcium Gluconate on Human Stool Flora>

Calcium gluconate, as an example of this invention, was administered to man and its effect on intestinal flora was evaluated.

Six healthy male adult volunteers (aged 28~56) were instructed to ingest calcium gluconate powder in a daily dose of 1.7 g once (after lunch) daily and the stool flora was determined at week 1 before intake, on the day of beginning of intake, at weeks 1 and 2 of intake, and weeks 1 and 2 of washout after intake by the same method as used in Test Example 3. The results are set forth in Table 22.

TABLE 22

| | Logarithm of the viable count in each gram of feces* The figure in parentheses denotes the percentage (%) of total count* | |
|---|---|---|
| Microorganism | Week 1 before intake | Day 0 of intake |
| Bifidobacterium | 9.5 ± 0.8 (17.7 ± 18.3) | 9.7 ± 0.7 (19.3 ± 19.3) |
| Bacteroidaceae | 10.3 ± 0.4 (45.0 ± 27.1) | 10.3 ± 0.2 (46.9 ± 21.5) |
| Eubacterium | 10.0 ± 0.2 (25.1 ± 11.8) | 10.1 ± 0.2 (22.8 ± 7.2) |
| C. perfringens (Welch's bacillus) | 6.7 ± 0.4 | 3.5 ± 0.5 |
| Enterobacteriaceae (inclusive of coliform bacteria) | 8.4 ± 1.1 | 8.3 ± 1.2 |
| Total viable count | 10.7 ± 0.2 (100) | 10.7 ± 0.1 (100) |

| | Logarithm of the viable count in each gram of feces* The figure in parentheses denotes the percentage (%) of total count* | |
|---|---|---|
| Microorganism | Week 1 of intake | Week 2 of intake |
| Bifidobacterium | 10.1 ± 0.3 (35.8 ± 24.0) | 9.9 ± 0.6 (30.1 ± 26.9) |
| Bacteroidaceae | 10.1 ± 0.6 (35.2 ± 24.5) | 10.3 ± 0.4 (43.6 ± 23.6) |
| Eubacterium | 10.0 ± 0.2 (22.9 ± 5.3) | 10.0 ± 0.3 (19.4 ± 6.9) |
| C. perfringens (Welch's bacillus) | 4.0 ± 0.8 | 4.7 ± 1.4 |
| Enterobacteriaceae (inclusive of coliform bacteria) | 8.4 ± 1.0 | 8.4 ± 1.1 |
| Total viable count | 10.7 ± 0.3 (100) | 10.8 ± 0.2 (100) |

| | Logarithm of the viable count in each gram of feces* The figure in parentheses denotes the percentage (%) of total count* | |
|---|---|---|
| Microorganism | Week 1 of washout | Week 2 of washout |
| Bifidobacterium | 9.7 ± 0.7 (32.5 ± 26.2) | 9.8 ± 0.8 (21.2 ± 18.9) |
| Bacteroidaceae | 10.0 ± 0.8 (38.9 ± 28.5) | 10.4 ± 0.2 (47.1 ± 17.6) |
| Eubacterium | 10.0 ± 0.2 (27.5 ± 5.9) | 10.1 ± 0.2 (25.6 ± 13.6) |
| C. perfringens (Welch's bacillus) | 3.0 ± 0.6 | 3.9 ± 2.1 |
| Enterobacteriaceae (inclusive of coliform bacteria) | 8.1 ± 1.1 | 8.2 ± 1.2 |
| Total viable count | 10.6 ± 0.3 (100) | 10.8 ± 0.2 (100) |

*Mean ± SD

It is apparent from Table 22 that calcium gluconate increased the intestinal population of bifidobacteria as compared with the pre-ingestion baseline.

Industrial Applicability

The bifidobacterium growth promotant of this invention provides a selective growth promoting effect on bifidobacteria and has excellent characteristics as a bifidus factor. Therefore, the bifidobacterium growth promotant of this invention can be used as it is or as added to various kinds of foods and beverages to provide functional foods and drinks and is, hence, of great value from the standpoint of health promotion.

We claim:

1. A salt-containing composition, comprising a bifidobacterium growth promoting amount of each of sodium chloride and a metal gluconate.

2. The salt-containing composition of claim 1, wherein said composition comprises about 40% or more of said metal gluconate.

3. The salt-containing composition of claim 1, wherein said composition comprises up to about 40% of said metal gluconate.

4. The salt-containing composition of claim 1, wherein said alkali metal gluconate is selected from the group consisting of sodium-, potassium-, calcium-, magnesium- zinc-, and copper gluconate.

5. A sweetener composition, comprising a bifidobacterium growth promoting amount of each of aspartame and a metal gluconate. copper gluconate.

6. The sweetener composition of claim 5, wherein said metal gluconate is present in an amount of not higher than about 1%.

7. The sweetener composition of claim 5, which further comprises an auxiliary component selected from the group consisting of an acidulate, other sweetener, condiment and excipient.

8. The sweetener composition of claim 5, wherein said metal gluconate is selected from the group consisting of sodium-, potassium-, calcium-, magnesium-, zinc- and copper gluconate.

* * * * *